(12) United States Patent
Mason et al.

(10) Patent No.: US 7,485,103 B2
(45) Date of Patent: Feb. 3, 2009

(54) ROTATIONAL HINGE ASSEMBLY FOR A KNEE BRACE HAVING AN OSTEOARTHRITIS TREATMENT FUNCTION

(75) Inventors: Bradley R. Mason, Rancho Santa Fe, CA (US); Aadel Al-Jadda, Encinitas, CA (US)

(73) Assignee: Breg, Inc., Vista, CA (US)

( * ) Notice: Subject to any disclaimer, the term of this patent is extended or adjusted under 35 U.S.C. 154(b) by 73 days.

(21) Appl. No.: 11/404,500

(22) Filed: Apr. 13, 2006

(65) Prior Publication Data

US 2007/0244419 A1 Oct. 18, 2007

(51) Int. Cl.
- A61F 5/00 (2006.01)
- A61F 5/37 (2006.01)
- A61F 13/00 (2006.01)
- A61B 19/00 (2006.01)

(52) U.S. Cl. .............. 602/16; 602/5; 602/23; 602/26; 128/846; 128/869; 128/882

(58) Field of Classification Search ............. 602/5, 602/16, 23, 26, 41–44, 61–63; 128/869, 128/882, 861; 16/354, 50, 221, 235, 238; 475/3, 10, 12, 55–56; 254/236

See application file for complete search history.

(56) References Cited

U.S. PATENT DOCUMENTS

| | | | |
|---|---|---|---|
| 401,933 A | 4/1889 | De Camp | |
| 2,711,167 A | 6/1955 | Rickard | |
| 3,669,105 A | 6/1972 | Castiglia | |
| 4,191,373 A | 3/1980 | Lancellotti | |
| 4,372,298 A | 2/1983 | Lerman | |
| 4,481,941 A | 11/1984 | Rolfes | |
| 4,599,998 A * | 7/1986 | Castillo | 602/16 |
| 4,940,045 A | 7/1990 | Cromartie | |
| 4,991,571 A | 2/1991 | Kausek | |
| 5,086,760 A | 2/1992 | Neumann et al. | |
| 5,277,698 A | 1/1994 | Taylor | |
| 5,458,565 A | 10/1995 | Tillinghast, III et al. | |
| 5,527,268 A | 6/1996 | Gildersleeve et al. | |
| 5,586,970 A | 12/1996 | Morris et al. | |
| 5,672,152 A | 9/1997 | Mason et al. | |
| 5,772,618 A * | 6/1998 | Mason et al. | 602/16 |
| 5,807,294 A * | 9/1998 | Cawley et al. | 602/26 |
| 5,827,208 A | 10/1998 | Mason et al. | |

(Continued)

*Primary Examiner*—Patricia Bianco
*Assistant Examiner*—Brandon Jackson
(74) *Attorney, Agent, or Firm*—Rodney F. Brown (57) ABSTRACT

A hinge assembly for a knee brace includes a screw seat, a screw seat gear, an adjustment screw, a condyle engagement member, and an adjustment actuator gear. The screw seat has a bore with an internal thread. The screw seat gear is positioned at an end of the screw seat and the screw seat rotates in response to rotation of the screw seat gear. The adjustment actuator gear engages the screw seat gear and the screw seat gear rotates in response to rotation of the adjustment actuator gear. The adjustment screw has an external thread that is threaded into the internal thread of the screw seat, thereby enabling outward or inward telescoping of the adjustment screw within the bore in response to rotation of the adjustment actuator gear. The adjustment screw is connected to the condyle engagement member, thereby enabling proximal displacement of the condyle engagement member in response to outward telescoping of the adjustment screw and enabling distal displacement of the condyle engagement member in response to inward telescoping of the adjustment screw.

20 Claims, 5 Drawing Sheets

U.S. PATENT DOCUMENTS

| | | | |
|---|---|---|---|
| 6,039,709 A * | 3/2000 | Bzoch | 602/26 |
| 6,666,837 B2 * | 12/2003 | Weihermuller | 602/16 |
| 6,752,755 B2 * | 6/2004 | Akiba | 600/127 |
| 6,752,775 B2 * | 6/2004 | Seligman et al. | 602/16 |
| 7,059,329 B2 * | 6/2006 | Mason et al. | 128/861 |
| 7,060,045 B2 * | 6/2006 | Mason et al. | 602/5 |
| 2005/0234376 A1 * | 10/2005 | Rossi et al. | 602/16 |

* cited by examiner

ROTATIONAL HINGE ASSEMBLY FOR A KNEE BRACE HAVING AN OSTEOARTHRITIS TREATMENT FUNCTION

TECHNICAL FIELD

The present invention relates generally to orthopedic braces, and more particularly to a knee brace having a rotational hinge assembly configured to enable treatment of osteoarthritis.

BACKGROUND OF THE INVENTION

Orthopedic braces embody a broad range of structures, each having the common purpose of supporting and/or stabilizing a skeletal joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury while the joint is rehabilitated.

Conventional orthopedic braces typically include a frame consisting of a plurality of rigid support members positioned adjacent to the body on either side of the skeletal joint being stabilized. The rigid support members are dynamically interconnected by one or more rotational hinges. Thus, a conventional knee brace typically includes a frame having a rigid upper support member positioned adjacent to the upper leg and a rigid lower support member positioned adjacent to the lower leg. A rotational hinge positioned adjacent to the knee dynamically interconnects the rigid upper and lower support members enabling controlled pivotal movement of the knee joint during user activity or rehabilitative therapy. The knee brace is typically secured to the leg by a plurality of straps.

One destabilizing condition of the knee joint is osteoarthritis, a degenerative disease that results in chronic pain to the subject when the knee joint is statically or dynamically loaded. Osteoarthritis is commonly the result of aging, knee joint overuse, or injury. Osteoarthritic pain is caused by an unbalanced loading on the medial or lateral compartment of the knee joint which closes the clearance space forming the compartment between the condyles of the femur and tibia. When there is contact of the condyles in the afflicted compartment of the knee joint, abrasion occurs at the contact surface producing pain in the joint. Wearing a knee brace on the affected leg is a common noninvasive means of treating osteoarthritis to reduce the pain associated therewith. The present invention recognizes the need for a knee brace which has an osteoarthritis treatment function.

Accordingly, it is an object of the present invention to provide a knee brace for treatment of osteoarthritis in the knee joint. More particularly, it is an object of the present invention to provide a rotational hinge assembly for a knee brace which treats osteoarthritis in the knee joint. It is a further object of the present invention to provide a rotational hinge assembly for a knee brace which applies a treatment force to the knee joint of the user. It is yet another object of the present invention to provide a rotational hinge assembly for a knee brace which applies an adjustable treatment force to the knee joint of the user. These objects and others are achieved by the invention described hereafter.

These objects and others are accomplished in accordance with the invention described hereafter.

SUMMARY OF THE INVENTION

The present invention is a hinge assembly for a knee brace comprising first and second screw seats, first and second screw seat gears, first and second adjustment screws, a condyle engagement member, and an adjustment actuator gear. Each screw seat has a bore with an internal thread in the bore. The first screw seat gear is positioned at an end of the first screw seat and the first screw seat rotates in response to rotation of the first screw seat gear. The second screw seat gear is positioned at an end of the second screw seat and the second screw seat rotates in response to rotation of the second screw seat gear. The adjustment actuator gear engages the first and second screw seat gears, which rotate in response to rotation of the adjustment actuator gear.

Each adjustment screw has an external thread. The first adjustment screw is positioned in the bore of the first screw seat with the external thread threaded into the internal thread, thereby enabling outward or inward telescoping of the first adjustment screw within the bore in response to rotation of the adjustment actuator gear. The second adjustment screw is positioned in the bore of the second screw seat with the external thread threaded into the internal thread, thereby enabling outward or inward telescoping of the second adjustment screw within the bore likewise in response to rotation of the adjustment actuator gear.

The first and second adjustment screws are connected to the condyle engagement member, thereby enabling proximal displacement of the condyle engagement member in response to outward telescoping of the first and second adjustment screws and enabling distal displacement of the condyle engagement member in response to inward telescoping of the first and second adjustment screws.

In accordance with one embodiment, the hinge assembly further comprises a hinge support plate connected to the first and second screw seats. The adjustment actuator gear rotatably engages the hinge support plate. The hinge support plate may alternatively be a first hinge support plate with the hinge assembly further comprising a second hinge support plate and a hinge cover plate.

In accordance with another embodiment, the hinge assembly further comprises an actuator wheel and a display actuator gear. The adjustment actuator gear and the display actuator gear are positioned on the actuator wheel and rotate in response to rotation of the actuator wheel. The hinge assembly may further comprise a display gear engaging the display actuator gear. The display gear rotates in response to rotation of the display actuator gear. The hinge assembly may still further comprise a manually rotatable adjustment wheel. The adjustment wheel is connected to the adjustment actuator gear and the adjustment actuator gear rotates in response to rotation of the actuator wheel.

In another characterization of the invention, the hinge assembly comprises the screw seat, screw seat gear, and adjustment screw. In accordance with one embodiment of this characterization, the hinge assembly further comprises the condyle engagement member. In accordance with another embodiment of this characterization, the hinge assembly further comprises the adjustment actuator gear.

In another characterization of the invention, the hinge assembly comprises the screw seat, screw seat gear, adjustment screw, condyle engagement member, and a displacement indicator. The displacement indicator displays a degree of proximal or distal displacement of the condyle engagement member. In accordance with one embodiment of this characterization, the displacement indicator includes the display gear.

The present invention will be further understood from the drawings and the following detailed description.

Embodiments of the invention are illustrated by way of example and not by way of limitation in the above-recited figures of the drawings in which like reference characters indicate the same or similar elements. It should be noted that common references to "an embodiment", "one embodiment", "an alternate embodiment", "a preferred embodiment", or the like herein are not necessarily references to the same embodiment.

DESCRIPTION OF PREFERRED EMBODIMENTS

There are a number of relative terms defined below which are used in the following description to distinguish various elements of a rotationally-hinged knee brace from one another, but which are not to be construed as limiting the scope of the present invention. The relative terms "medial" and "lateral" describe the relative proximity of certain elements to the central longitudinal axis of the body of the user when the knee brace is secured to a leg of the user. A "medial" element is closer to the central longitudinal axis of the body, while a "lateral" element is further from the central longitudinal axis of the body.

The terms "proximal" and "distal" describe the relative proximity of certain elements to the knee joint when the knee brace is secured to the leg of the user. A "proximal" element is closer to the knee joint, while a "distal" element is further from the knee joint. The terms "upper" and "lower" describe the position of certain elements as being either above or below the rotational hinges of the brace and correspondingly either above or below the knee joint. An "upper" element is above the rotational hinges and knee joint, while a "lower" element is below the rotational hinges and knee joint.

The relative terms "posterior" and "anterior" characterize certain elements of the knee brace and, in particular, describe the orientation of the given element relative to the central longitudinal axis of the body of the user when the brace is secured to the leg of the user. A "posterior" element is positioned behind the central longitudinal axis of the body in correspondence with the posterior of the body, while an "anterior" element is positioned in front of the central longitudinal axis of the body in correspondence with the posterior of the body.

Figure 1:
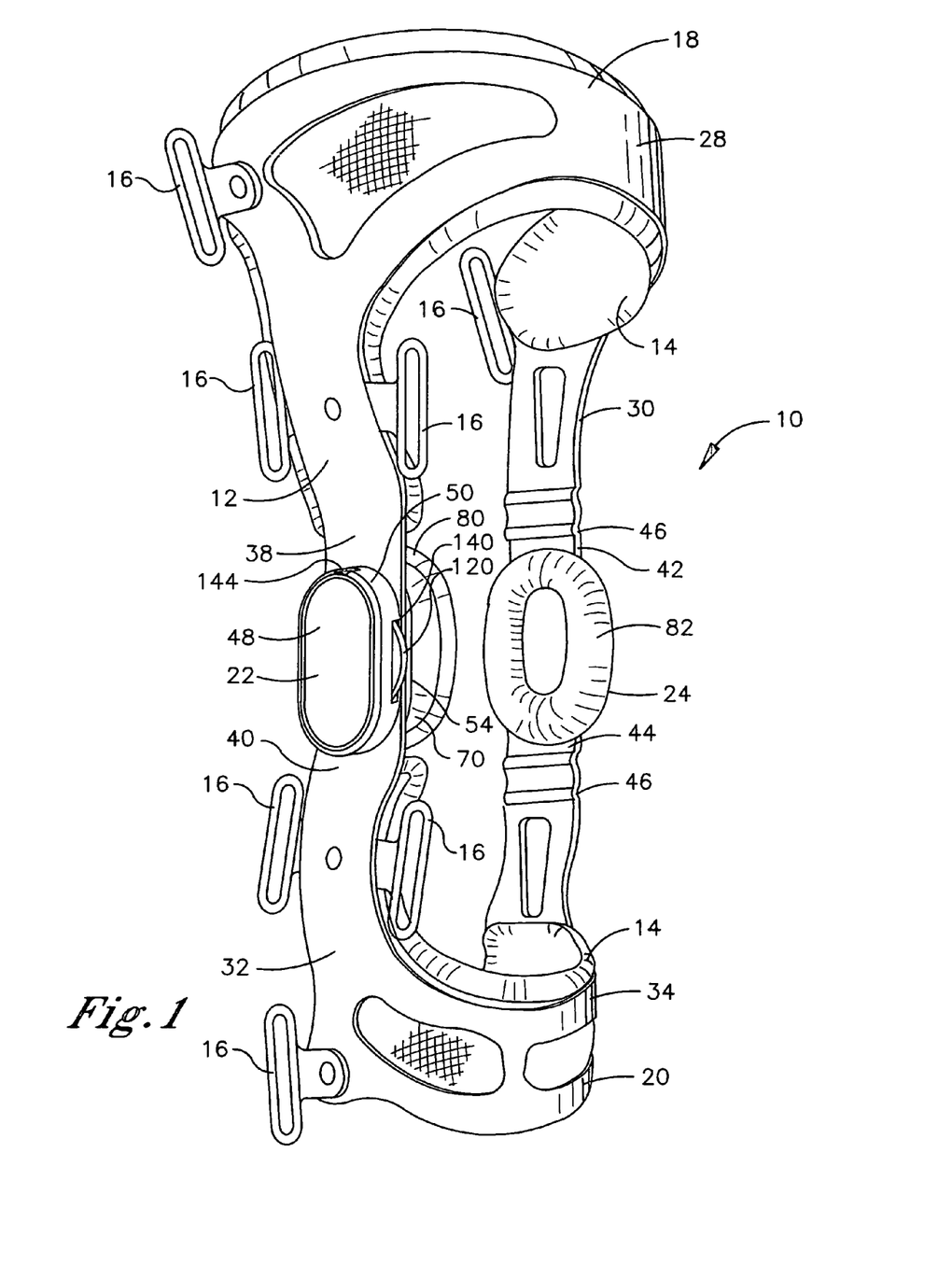
FIG. 1 is a perspective view of a knee brace having a rotational hinge assembly which enables an osteoarthritis treatment function.
Figure 2A:
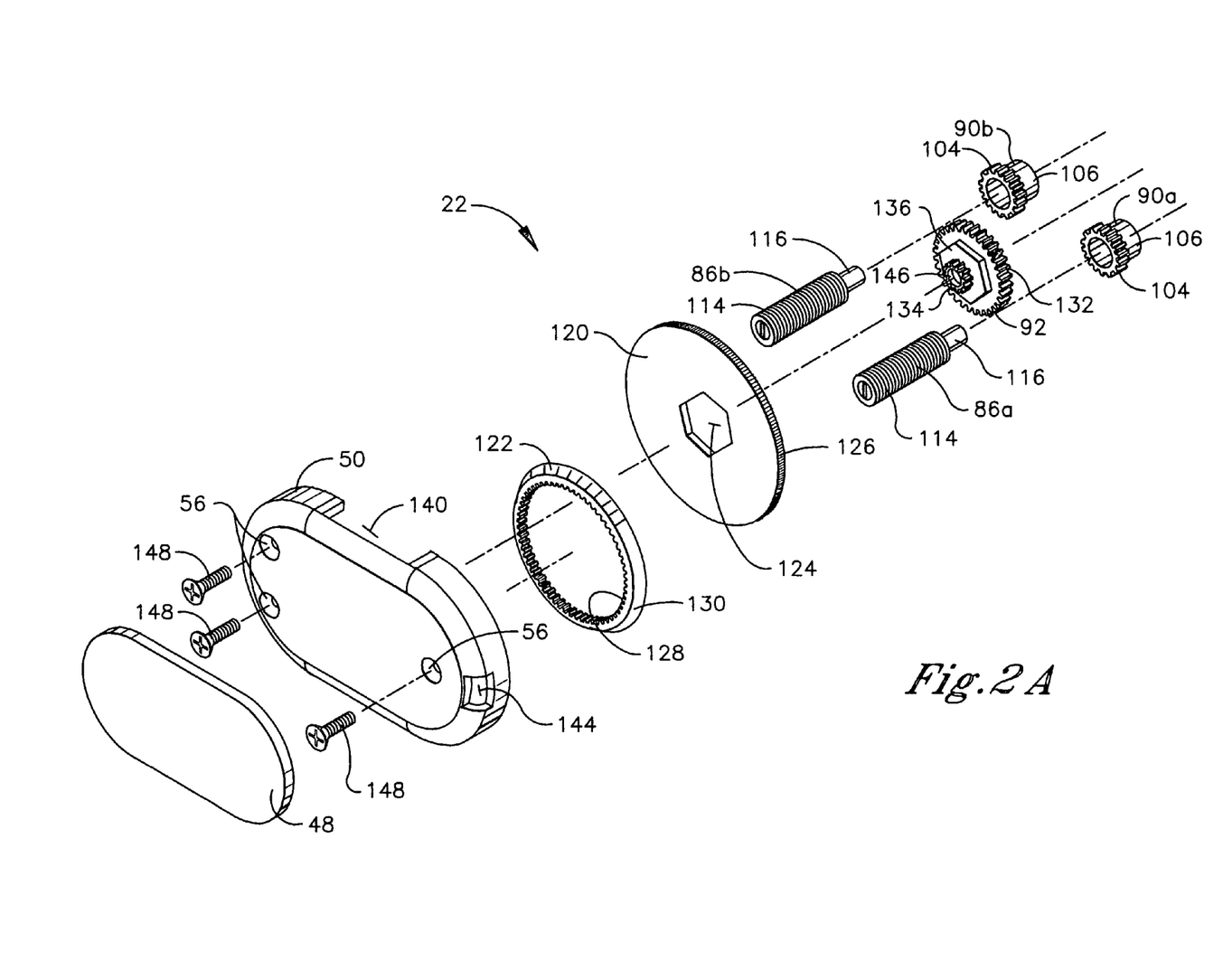
FIGS. 2A, 2B and 2C are an exploded perspective view of the rotational hinge assembly of FIG. 1 which enables an osteoarthritis treatment function.
Figure 2B:
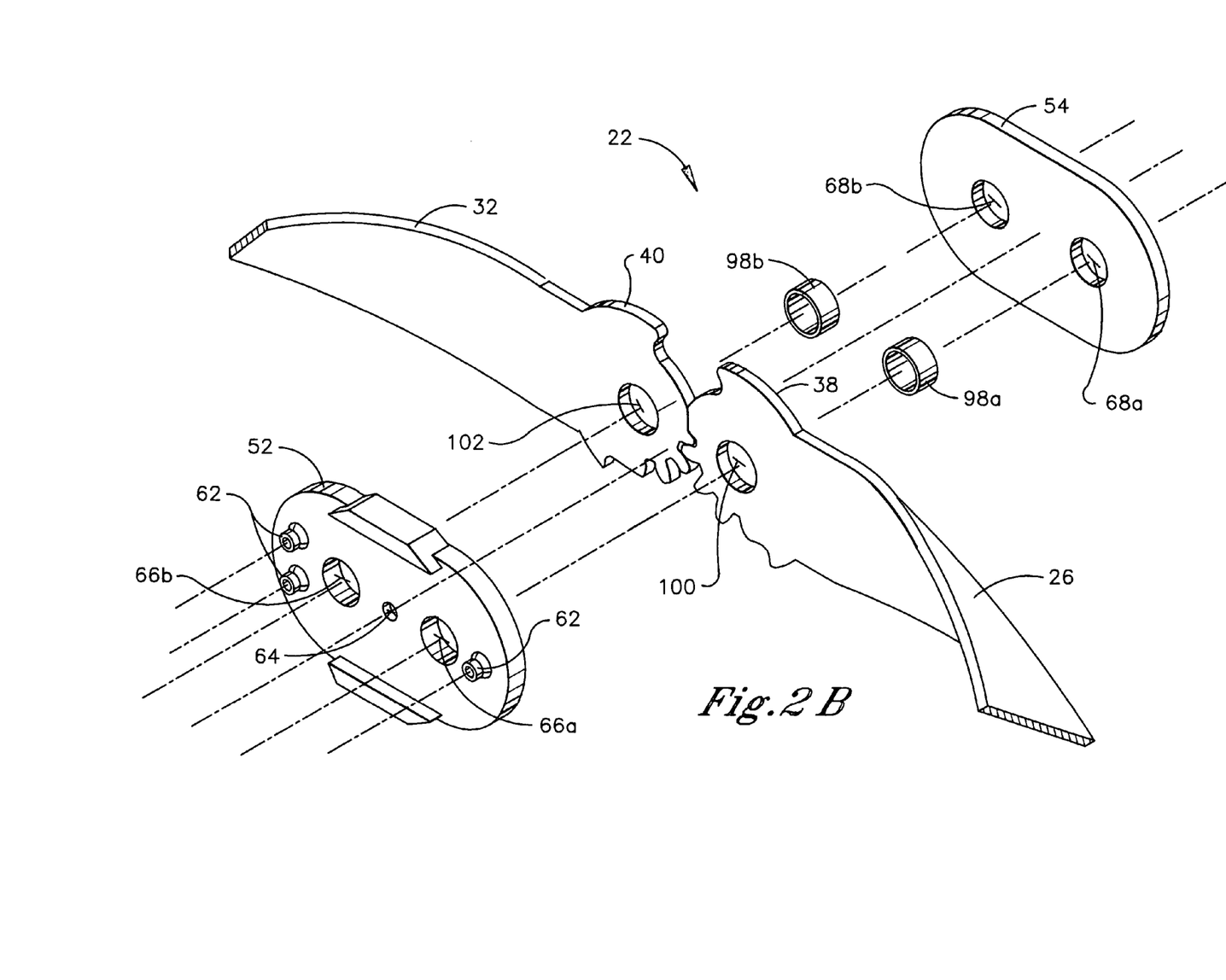
Figure 2C:
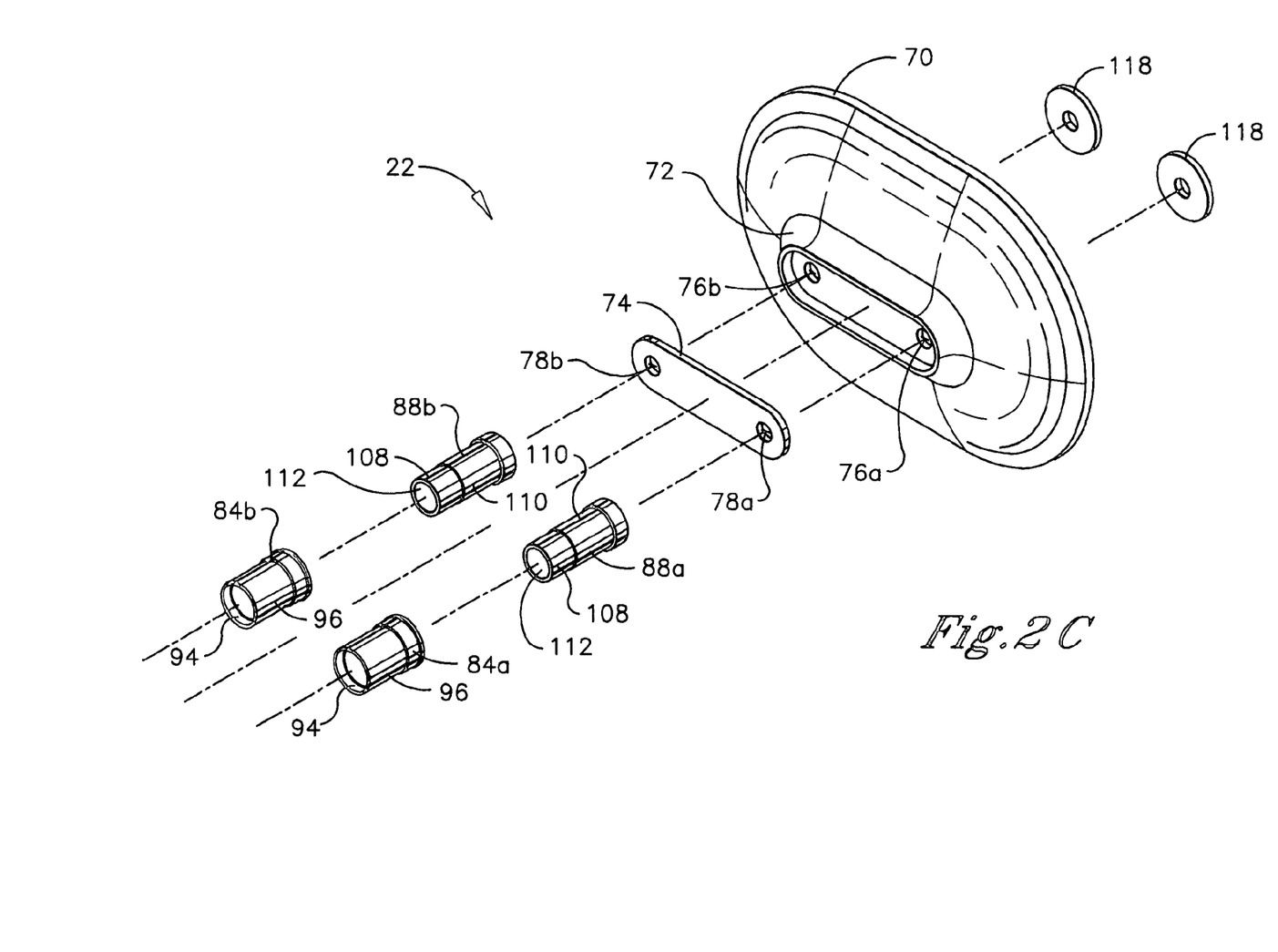
Figure 3:
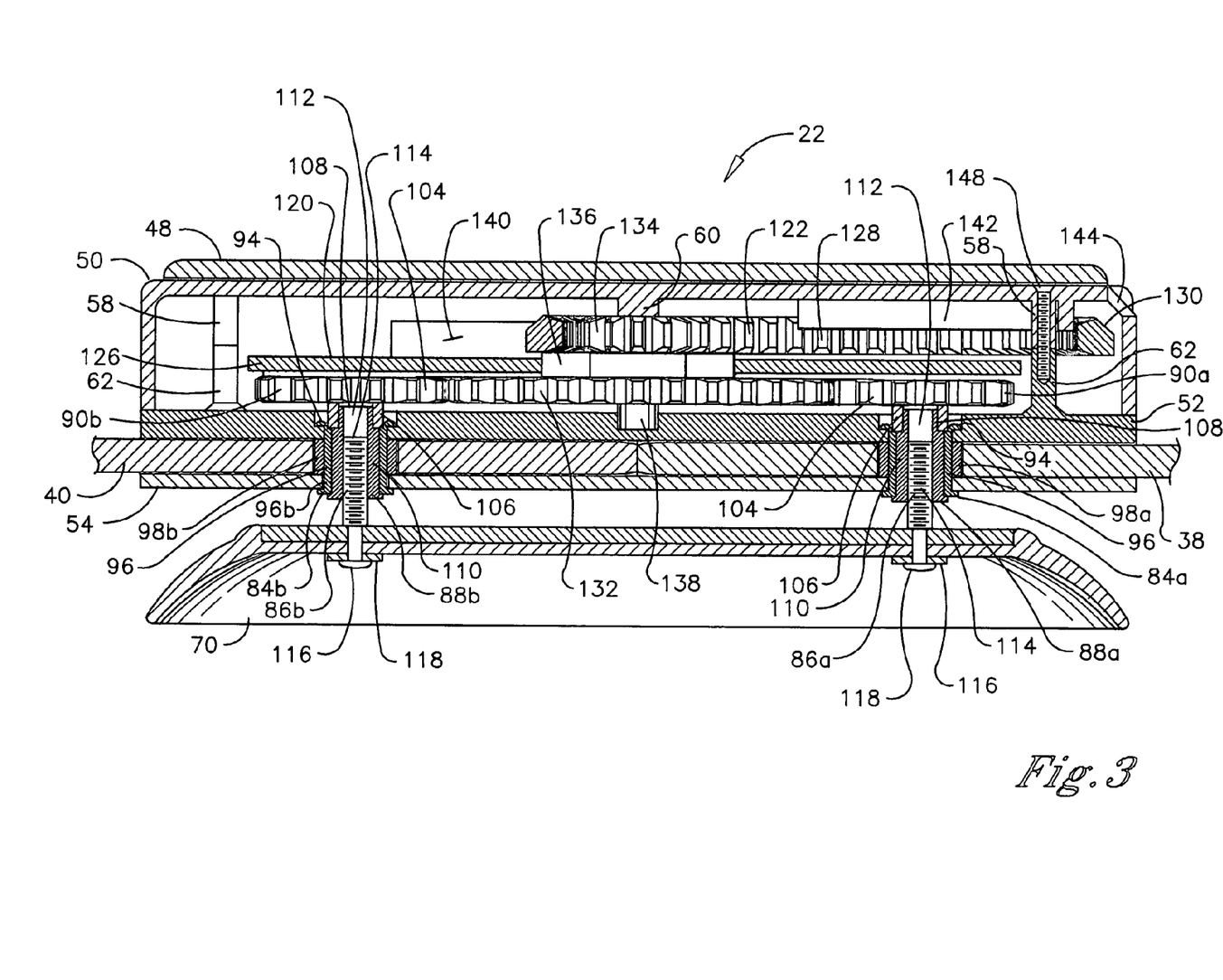
FIG. 3 is a cross-sectional view of the rotational hinge assembly of FIG. 1 which enables an osteoarthritis treatment function.

Referring initially to FIG. 1, a rotationally-hinged knee brace is shown and generally designated 10. For purposes of illustration, the knee brace 10 is configured for securing to a right leg of a user. However, it is readily apparent to the skilled artisan from the teaching provided herein that the knee brace 10 can be adapted for securing to the opposite leg of the user.

In general, rotationally-hinged knee braces have a number of common elements, including a rotationally-hinged frame, padding, and a plurality of straps and strap retainers. As such, the rotationally-hinged knee brace 10 is shown to include a rotationally-hinged frame 12, padding 14, and strap retainers 16. However, the straps associated with the strap retainers 16 are omitted for clarity. Nevertheless, the placement and function of the omitted straps on the knee brace 10 is readily apparent to the skilled artisan.

The present embodiment of the rotationally-hinged frame 12 includes an upper frame assembly 18, a lower frame assembly 20, a lateral rotational hinge assembly 22, and a medial rotational hinge assembly 24. The upper frame assembly 18 comprises in combination a lateral upper longitudinal support 26, an upper cuff 28, and a medial upper longitudinal support 30. The lower frame assembly 20 similarly comprises in combination a lateral lower longitudinal support 32, a lower cuff 34, and a medial lower longitudinal support 36.

The upper and lower frame assemblies 18, 20 are laterally connected to one another by the lateral rotational hinge assembly 22 which is positioned at a central horizontal rotational axis of the rotationally-hinged frame 12. In particular, the lateral rotational hinge assembly 22 in cooperation with the lateral upper and lower longitudinal supports 26, 32 effects rotational connection of the upper and lower frame assemblies 18, 20. The lateral upper longitudinal support 26 is an elongate arm having a lateral upper hinge end 38 and the lateral lower longitudinal support 32 is similarly constructed having a lateral lower hinge end 40. The lateral upper and lower hinge ends 38, 40 are specifically configured to cooperatively engage one another and to engage the lateral rotational hinge assembly 22 in a manner described below. Thus, the lateral rotational hinge assembly 22 enables rotational displacement of the lateral upper and lower longitudinal supports 26, 32 about the central rotational axis of the rotationally-hinged frame 12 between positions of extension and flexion.

The upper and lower frame assemblies 18, 20 are similarly medially connected to one another by the medial rotational hinge assembly 24 positioned at the central horizontal rotational axis of the rotationally-hinged frame 12. In particular, the medial rotational hinge assembly 24 effects rotational connection of the upper and lower frame assemblies 18, 20 in cooperation with the medial upper and lower longitudinal supports 30, 36. The medial upper longitudinal support 30 is an elongate arm having a medial upper hinge end 42 and the medial lower longitudinal support 36 is similarly constructed having a medial lower hinge end 44. The medial upper and lower hinge ends 42, 44 are specifically configured to cooperatively engage one another and to engage the medial rotational hinge assembly 24 in a manner described below. Thus, the medial rotational hinge assembly 24 enables rotational displacement of the medial upper and lower longitudinal supports 30, 36 about the central rotational axis of the rotationally-hinged frame 12 between positions of extension and flexion.

In a preferred embodiment, the lateral rotational hinge assembly 22 has specific structure which enables an osteoarthritis treatment function in accordance with the teaching described in greater detail hereafter. In contrast, the medial rotational hinge assembly 24 is preferably a conventional rotational hinge assembly which lacks certain structure of the lateral rotational hinge assembly 22 that enables the osteoarthritis treatment function. As such, the lateral and medial frame assemblies of the rotationally-hinged frame 12 have different constructions and performance characteristics.

A conventional rotational hinge assembly having utility herein as the medial rotational hinge assembly 24 is disclosed in U.S. Pat. No. 5,772,618, which is incorporated herein by reference. Exemplary additional prior art hinges are disclosed in U.S. Pat. Nos. 401,933; 4,481,941; 5,672,152; and 5,827, 208. In accordance with a preferred embodiment, the medial rotational hinge assembly 24 is essentially rigid (i.e., inflexible) in a mediolateral direction (i.e., side-to-side).

The rotationally-hinged frame 12 has been characterized above as being divided into upper and lower frame assemblies 18, 20. The rotationally-hinged frame 12 may be alternately be characterized as being divided into a lateral frame assembly and a medial frame assembly. The lateral frame assembly is comprised of the lateral upper longitudinal support 26, lateral rotational hinge assembly 22, and lateral lower longitudinal support 32 in serial combination. The medial frame assembly is comprised of the medial upper longitudinal support 30, medial rotational hinge assembly 24, and medial lower longitudinal support 36 in serial combination.

The rotationally-hinged frame 12 of the present embodiment is further characterized as having asymmetrical or unbalanced flexibility characteristics. In particular, the medial frame assembly is substantially more flexible than the lateral frame assembly in a mediolateral or twisting direction. The increased flexibility of the lateral frame assembly is attributable to differences between the construction of the lateral upper and lower longitudinal supports 26, 32 and the medial upper and lower longitudinal supports 30, 36. Whereas, the lateral upper and lower longitudinal supports 26, 32 each have a uniform and rigid construction, the medial upper and lower longitudinal supports 30, 36 each have a segmented construction which provides each with a non-uniform degree of rigidity (and conversely with a non-uniform degree of flexibility) along its length.

The flexibility of the medial upper and lower longitudinal supports 30, 36 is the result of one or more offset hinges 46 structurally integrated into each of the medial longitudinal supports 30, 36. Each offset hinge 46 is a more flexible connective segment which extends between and is fixably attached to the remaining more rigid segments of each medial longitudinal support 30, 36. The offset hinge 46 is sufficiently flexible to enable manual displacement of each medial longitudinal support 30, 36 in the mediolateral or twisting direction about the offset hinge 46. As such, the term "offset hinge" is used herein to designate a flexible connective segment which extends between and connects two more rigid segments and which enables the two more rigid segments to assume a non-linear orientation with respect to one another, thereby creating an offset angle between them when they are displaced about the connective segment.

A frame for a knee brace exhibiting unbalanced flexibility characteristics by means of offset hinges in the manner of the above-described rotationally-hinged frame 12 is disclosed in commonly-owned U.S. patent application Ser. No. 11/040,814 filed on Jan. 22, 2005, which is incorporated herein by reference. It is, nevertheless, understood that the rotationally-hinged frame 12 shown and described herein is but an example of a type of frame within which a rotational hinge assembly having an osteoarthritis treatment function has utility. As such, a rotational hinge assembly of the present invention having an osteoarthritis treatment function is not limited to use within any specific type of frame for a knee brace but is generally applicable to most conventional types of frames for knee braces.

Referring to FIGS. 2A, 2B and 2C and FIG. 3, the lateral rotational hinge assembly 22 having an osteoarthritis treatment function is described and shown in greater detail. The lateral rotational hinge assembly 22 comprises a plurality of hinge plates connected in series. The serially-connected hinge plates include a hinge face plate 48, a hinge cover plate 50, a distal hinge support plate 52, and a proximal hinge support plate 54. Each hinge plate has an essentially planar configuration and the hinge plates 48, 50, 52, 54 are serially aligned essentially parallel to one another. The distal hinge support plate 52 and proximal hinge support plate 54 are both formed from a relatively rigid high-strength material, which enhances the structural integrity of the lateral rotational hinge assembly 22. In accordance with one embodiment, the distal hinge support plate 52 is formed from a rigid injection molded plastic and the proximal hinge support plate 54 is formed from a rigid metal. An exemplary proximal hinge support plate construction is disclosed in U.S. Pat. No. 5,772,618, wherein a metal plate is encased in a friction-reducing plastic sheath by insert molding.

A plurality of fastener apertures 56 extend through the hinge cover plate 50 and open into a plurality of corresponding bosses 58 proximally extending from the proximal face of the hinge cover plate 50. A centrally-mounted positioning nub 60 also proximally extends from the proximal face of the hinge cover plate 50. A plurality of corresponding internally-threaded bosses 62 distally extend from the distal face of the distal hinge support plate 52. The bosses 62 are aligned with the fastener apertures 56 and bosses 58 of the hinge cover plate 50. A centrally-positioned circular indent 64 is also formed in the distal face of the distal hinge support plate 52. A circular upper internal pivot opening 66a and a similarly-sized circular lower internal pivot opening 66b extend through the distal hinge support plate 52 on either side of the indent 64. The upper and lower internal pivot openings 66a, 66b align with correspondingly positioned upper and lower external pivot openings 68a, 68b, respectively, which extend through the proximal external hinge plate 54.

The lateral rotational hinge assembly 22 further comprises a lateral condyle engagement member 70 which has a proximal face with a concave cup configuration shaped to conform to the contours of a knee condyle. The condyle engagement member 70 is preferably formed from a stiffened yet pliant resilient material such as a stiff plastic. The condyle engagement member 70 is positioned adjacent to the proximal face of the proximal external hinge plate 54 and is essentially parallely aligned therewith. The distal face of the condyle engagement member 70 has a raised oval-shaped ring 72 formed thereon in alignment with the central longitudinal axis of the condyle engagement member 70. A condyle bar 74 dimensioned in correspondence with the ring 72 is additionally provided for positioning within the ring 72. The condyle bar 74 is preferably formed from a material more rigid than the condyle engagement member 70, such as a rigid metal, and provides increased structural integrity to the condyle engagement member 70 at its central longitudinal axis.

An upper engagement member fastener aperture 76a and a lower engagement member fastener aperture 76b extend through the condyle engagement member 70 at spaced apart positions within the ring 72. The upper engagement member fastener aperture 76a and lower engagement member fastener aperture 76b align with the upper and lower internal pivot openings 66a, 66b and the upper and lower external pivot openings 68a, 68b, respectively. An upper bar fastener aperture 78a and a lower bar fastener aperture 78b similarly extend through the condyle bar 74 and align with the upper and lower engagement member fastener apertures 76a, 76b, respectively.

A lateral condyle pad 80 (shown in FIG. 1) is preferably fitted over the proximal face of the lateral condyle engagement member 70 to cushion the knee condyle of the user from the lateral condyle engagement member 70. The condyle pad 80 is fastened or otherwise attached to proximal face of the lateral condyle engagement member 70 in an essentially permanent manner by conventional means, such as an adhesive, or in a selectively detachable manner by conventional means such as releasable hook and loop fasteners commercially available under the trade name "VELCRO". The condyle pad 80 is a thickened continuous cushion formed from a conventional pliant padding material which has limited compressibility. An exemplary condyle pad 80 is a foam cushion. Alternatively, the condyle pad 80 is a bladder containing a fluid or a fluid-like material having limited compressibility, such as a pneumatic bladder or gel-filled bladder.

The medial rotational hinge assembly 24 likewise includes a medial condyle engagement member (not shown) having substantially the same construction and function as the lateral condyle engagement member 70 of the lateral rotational hinge assembly 22. A medial condyle pad 82 (shown in FIG. 1) is preferably similarly fitted over the proximal face of the medial condyle engagement member and has substantially the same construction and function as the lateral condyle pad 80. The lateral and medial condyle engagement members and their associated condyle pads 80, 82 additionally function to maintain a close fit of the rotationally-hinged frame 12 with the knee joint during use.

The rotational hinge assembly 22 further comprises a rotational hinge adjustment mechanism which includes upper and lower plate connectors 84a, 84b, upper and lower adjustment screws 86a, 86b, upper and lower screw seats 88a, 88b, upper and lower screw seat gears 90a, 90b, and an actuator wheel 92. All of the above-recited components 84-92 of the rotational hinge adjustment mechanism are preferably fabricated from a high-strength rigid material such as steel.

The upper and lower plate connectors 84a, 84b each has a tubular configuration including a distal end 94 which is deformable into a rivet head and a body 96 which has an inside diameter. The upper plate connector 84a has an outside diameter sized such that the upper plate connector 84a fits into the upper internal and external pivot openings 66a, 68a and is fixably attachable to the distal hinge support plate 52 and proximal hinge support plate 54 at the openings 66a, 68a. The lower plate connector 84b similarly has an outside diameter sized such that the lower plate connector 84b fits into the lower internal and external pivot openings 66b, 68b and is fixably attachable to the distal hinge support plate 52 and proximal hinge support plate 54 at the pivot openings 66b, 68b. As such, the upper and lower plate connectors 84a, 84b function to fixably connect the distal hinge support plate 52 and the proximal hinge support plate 54 to one another.

An upper bushing 98a extends between the distal hinge support plate 52 and the proximal hinge support plate 54 at the upper internal and external pivot openings 66a, 68a, respectively. A lower bushing 98b correspondingly extends between the distal hinge support plate 52 and the proximal hinge support plate 54 at the lower internal and external pivot openings 66b, 68b, respectively. The upper and lower bushings 98a, 98b each has a tubular configuration. The upper bushing 98a has an inside diameter sized such that the upper bushing 98a fits around the body 96 of the upper plate connector 84a. The upper bushing 98a further has an outside diameter sized such that the upper bushing 98a does not fit into the upper internal and external pivot openings 66a, 68a, but fits into an upper end pivot opening 100 which extends through the lateral upper hinge end 38 of the lateral upper longitudinal support 26.

The lower bushing 98b similarly has an inside diameter sized such that the lower bushing 98b fits around the body 96 of the lower plate connector 84b. The lower bushing 98b further has an outside diameter sized such that the lower bushing 98b does not fit into the lower internal and external pivot openings 66b, 68b, but fits into a lower end pivot opening 102 which extends through the lateral lower hinge end 40 of the lateral lower longitudinal support 32. As such, the upper and lower bushings 98a, 98b function as spacers between the distal hinge support plate 52 and the proximal hinge support plate 54 and additionally function as the rotational pivots about which the upper and lower frame assemblies 18, 20 rotate.

The upper and lower screw seat gears 90a, 90b each has a tubular configuration including a distal end 104 with gear teeth encircling its outside perimeter and an externally and internally smooth proximal end 106 having an outside and an inside diameter. The upper and lower screw seats 88a, 88b each has a tubular configuration including an externally smooth distal end 108 having a reduced outside diameter relative to the outside diameter of the remaining body 110 of the screw seat 88a, 88b. Each upper and lower screw seat 88a, 88b further includes an internally-threaded bore 112 extending therethrough having an inside diameter. The upper and lower adjustment screws 86a, 86b each has a cylindrical configuration including an externally-threaded body 114 having an outside diameter and further including a smooth proximal end 116 which is deformable into a rivet head and which has an outside diameter less than the outside diameter of the body 114.

The outside diameter and external thread of the body 114 of the upper adjustment screw 86a and the inside diameter and internal thread of the bore 112 of the upper screw seat 88a are correspondingly sized such the body 114 screws into the bore 112. The proximal end 116 of the upper adjustment screw 86a is sized to proximally extend from the proximal end of the bore 112, through the upper bar fastener aperture 78a and through the upper engagement member fastener aperture 76a where the proximal end 116 is received by a washer 118.

The outside diameter of the proximal end 106 of the upper screw seat gear 90a is sized to fit within the upper internal pivot opening 66a. The inside diameter of the proximal end 106 and the outside diameter of the distal end 108 of the upper screw seat 88a are correspondingly sized such that the distal end 108 fits into the proximal end 106. The outside diameter of the body 110 of the upper screw seat 88a and the inside diameter of the upper plate connector 84a are correspondingly sized such that the body 110 fits into the upper plate connector 84a.

The outside diameter and thread of the body 114 of the lower adjustment screw 86b and the inside diameter and thread of the bore 112 of the lower screw seat 88b are correspondingly sized such the body 114 screws into the bore 112. The proximal end 116 of the lower adjustment screw 86b is sized to proximally extend from the proximal end of the bore 112, through the lower bar fastener aperture 78b and through the lower engagement member fastener aperture 76b where the proximal end 116 is received by a washer 118.

The outside diameter of the proximal end 106 of the lower screw seat gear 90b is sized to fit within the lower internal pivot opening 66b. The inside diameter of the proximal end 106 and the outside diameter of the distal end 108 of the lower screw seat 88b are correspondingly sized such that the distal end 108 fits into the proximal end 106. The outside diameter of the body 110 of the lower screw seat 88b and the inside diameter of the lower plate connector 84b are correspondingly sized such that the body 110 fits into the lower plate connector 84b.

The rotational hinge adjustment mechanism further includes an adjustment wheel 120 and a display gear 122. The adjustment wheel 120 is preferably fabricated from a high-strength rigid material, such as steel, and has a hex-shaped central mounting opening 124 and a knurled periphery 126.

The display gear 122 has a ring configuration with gear teeth mounted on its inside face 128 and position reference markings displayed on its outside face 130.

The actuator wheel 92 includes a proximally-positioned adjustment actuator gear 132, a distally-positioned display actuator gear 134, an intervening hex-shaped male mounting member 136, and a centrally-mounted proximally-extending positioning nub 138. The adjustment actuator gear 132 has an outside diameter sized for positioning between and engaging the upper and lower screw seat gears 90a, 90b. As such, the gear teeth of the adjustment actuator gear 132 are sized and configured to simultaneously and cooperatively mesh with the gear teeth of the upper and lower screw seat gears 90a, 90b. The male mounting member 136 and mounting opening 124 of the adjustment wheel 120 are correspondingly sized and configured such that the mounting member 136 fits into the mounting opening 124. The adjustment wheel 120 has a diameter sized such that the periphery 126 of the adjustment wheel 120 extends through wheel openings 140 provided in posterior and anterior sides of the hinge cover plate 50. The positioning nub 138 is sized to be received in the circular indent 64 of the distal hinge support plate 52.

The display gear 122 has an outside diameter sized to be fully contained under the hinge cover plate 50. A raised arcuate guide rail 142 is formed on the proximal face of the hinge cover plate 50, which engages the outside face 130 of the display gear 122 to maintain a desired off-center position of the display gear 122 relative to the hinge cover plate 50 when the hinge cover plate 50 is positioned over the display gear 122. A display window 144 is also formed in the hinge cover plate 50, which enables a user to view the position reference markings on the outside face 130 of the display gear 122 through the hinge cover plate 50. As such, the display gear 122 and display window 144 cooperatively function as a displacement indicator for the lateral condyle engagement member 70 in a manner described hereafter. The gear teeth of the display gear 122 are sized and configured to cooperatively mesh with the gear teeth of the display actuator gear 134. A circular indent 146 is centrally formed in the distal face of the display actuator gear 134, which is sized to receive the positioning nub 60 of the hinge cover plate 50.

The above-described rotation hinge assembly 22 is assembled by placing the upper and lower bushings 98a, 98b in the upper and lower end pivot openings 100, 102 formed through the lateral upper and lower hinge ends 38, 40 of the lateral upper and lower longitudinal supports 26, 32, respectively. The distal hinge support plate 52 is positioned on the distal side of the upper and lower bushings 98a, 98b and the lateral upper and lower hinge ends 38, 40 of the lateral upper and lower longitudinal supports 26, 32, while the proximal hinge support plate 54 is positioned on the proximal side thereof. The upper and lower screw seats 88a, 88b are nested in the upper and lower plate connectors 84a, 84b, respectively.

The distal end 94 of the upper plate connector 84a is distally displaced through the upper external opening 68a of the proximal hinge support plate 54, through the upper bushing 98a, and into the upper internal pivot opening 66a of the distal hinge support plate 52. The upper plate connector 84a is fixably attached to the proximal hinge support plate 54 by press fitting the upper plate connector 84a into the upper external opening 68a. The upper plate connector 84a is fixably attached to the distal hinge support plate 52 by deforming the distal end 94 into a rivet head extending over the distal edge of the upper internal pivot opening 66a, while the distal end 108 of the upper screw seat 88a distally extends out of the upper internal pivot opening 66a.

The distal end 94 of the lower plate connector 84b, 88b is similarly distally displaced through the lower external opening 68b of the proximal hinge support plate 54, through the lower bushing 98b, and into the lower internal pivot opening 66b of the distal hinge support plate 52. The lower plate connector 84b is fixably attached to the proximal hinge support plate 54 by press fitting the lower plate connector 84b into the lower external opening 68b. The lower plate connector 84b is fixably attached to the distal hinge support plate 52 by deforming the distal end 94 into a rivet head extending over the distal edge of the lower internal pivot opening 66b, while the distal end 108 of the lower screw seat 88b distally extends out of the lower internal pivot opening 66b.

The proximal end 116 and body 114 of the upper adjustment screw 86a are proximally displaced through the upper internal pivot opening 66a of the distal hinge support plate 52 and into the bore 112 of the upper screw seat 88a. The body 114 is threaded into the bore 112 until the proximal end 116 proximally extends out of the bore 112. The condyle bar 74 is seated in the ring 72 of the condyle engagement member 70 and the proximal end 116 of the upper adjustment screw 86a is proximally displaced through the upper bar and engagement member fastener apertures 78a, 76a. The washer 118 is placed on the proximal end 116 and the proximal end 116 is deformed into a rivet head extending over the proximal edge of the upper engagement member fastener aperture 76a to fixably attach the upper adjustment screw 86a to the condyle engagement member 70.

The proximal end 116 and body 114 of the lower adjustment screw 86b are similarly proximally displaced through the lower internal pivot opening 66b of the distal hinge support plate 52 and into the bore 112 of the lower screw seat 88b. The body 114 is threaded into the bore 112 until the proximal end 116 proximally extends out of the bore 112. The condyle bar 74 is seated in the ring 72 of the condyle engagement member 70 and the proximal end 116 of the lower adjustment screw 86b is proximally displaced through the lower bar and engagement member fastener apertures 78b, 76b. The washer 118 is placed on the proximal end 116 and the proximal end 116 is deformed into a rivet head extending over the proximal edge of the lower engagement member fastener aperture 76b to fixably attach the lower adjustment screw 86b to the condyle engagement member 70.

The proximal end 106 of the upper screw seat gear 90a is press fitted onto the distal end 108 of the upper screw seat 88a so that the proximal end 106 extends into the upper internal pivot opening 66a. Press fitting the proximal end 106 onto the distal end 108 causes the upper screw seat gear 90a and upper screw seat 88a to rotate in unison when the upper screw seat gear 90a is rotationally displaced in a manner described hereafter.

The proximal end 106 of the lower screw seat gear 90b is similarly press fitted onto the distal end 108 of the lower screw seat 88b so that the proximal end 106 extends into the lower internal pivot opening 66b. Press fitting the proximal end 106 onto the distal end 108 causes the lower screw seat gear 90b and lower screw seat 88b to rotate in unison when the lower screw seat gear 90b is rotationally displaced in a manner described hereafter.

The actuator wheel 92 is mounted on the distal face of the distal hinge support plate 52 with the positioning nub 138 seated in the indent 64 such that the gear teeth of the adjustment actuator gear 132 cooperatively mesh with the gear teeth of the upper and lower screw seat gears 90a, 90b. The adjustment wheel 120 is fixably attached to the actuator wheel 92 by distally displacing the actuator gear 134 through the mounting opening 124 of the adjustment wheel 120 and press fitting the mounting member 136 of the actuator wheel 92 into the mounting opening 124. The display gear 122 is positioned over the adjustment wheel 120 such that the gear teeth on the inside face 128 of the display gear 122 cooperatively mesh with the gear teeth of the display actuator gear 134 which extends distally through mounting opening 124.

The hinge cover plate 50 is mounted over the display gear 122 such that the outside face 130 of the display gear 122 engages the guide rail 142, the positioning nub 60 is seated in the indent 146, and the bosses 58 on the hinge cover plate 50 align with the corresponding bosses 62 on the distal hinge support plate 52. A fastener screw 148 is proximally displaced though each fastener aperture 56 and screwed into the correspondingly aligned bosses 62 to securely attach the hinge cover plate 50 to the distal hinge support plate 52. The periphery 126 of the adjustment wheel 120 extends through wheel openings 140 of the hinge cover plate 50 and the position reference markings on the display gear 122 are visible to the user through the display window 144 after the hinge cover plate 50 is attached to the distal hinge support plate 52.

Assembly of the rotation hinge assembly 22 is completed by affixing the smooth continuous hinge face plate 48 to the distal face of the hinge cover plate 50 to cover the fastener apertures 56 and the heads of the fastener screws 148. The hinge plates 48, 50 are affixed to one another by conventional means such as by gluing.

Method of Operation

Adjustment of the rotation hinge assembly 22 is effected either when the knee brace 10 is mounted on the leg of a user or alternatively when the knee brace 10 is unmounted. In particular, adjustment is effected by manually engaging the periphery 126 of the adjustment wheel 120 extending through the wheel openings 140 of the hinge cover plate 50 and rotationally displacing the adjustment wheel 120 in either a first direction or an opposite second direction, wherein the first and second directions correspond to clockwise and counter-clockwise directions or vice versa.

Rotational displacement of the adjustment wheel 140 in the first direction causes rotation of the attached actuator wheel 92 as well as the integral adjustment and display actuator gears 132, 134 in the first direction. Rotation of the adjustment actuator gear 132 in the first direction causes rotation of both the upper and lower screw seat gears 90a, 90b as well as the fixably joined upper and lower screw seats 88a, 88b, respectively, in the second direction. Rotation of the upper and lower screw seats 88a, 88b in the second direction causes rotational displacement of the internal threads in the bores 112 of the upper and lower screw seats 88a, 88b relative to the external threads on the bodies 114 of the upper and lower adjustment screws 86a, 86b, respectively. Rotational displacement of the internal threads on the bodies 114 translates to linear displacement of the upper and lower adjustment screws 86a, 86b in the proximal direction from a lateral position relative to the upper and lower screw seats 88a, 88b. Linear displacement of the upper and lower adjustment screws 86a, 86b in the proximal direction from the lateral position is correspondingly relative to the distal and proximal hinge support plates 52, 54, to which the upper and lower screw seats 88a, 88b are connected. Proximal linear displacement from the lateral position is alternately termed outward telescoping of the upper and lower adjustment screws 86a, 86b within the bores 112 of the upper and lower screw seats 88a, 88b, respectively.

Proximal linear displacement of the upper and lower adjustment screws 86a, 86b from the lateral position causes corresponding proximal linear displacement of the condyle engagement member 70 from a lateral position, to which the proximal ends 116 of the upper and lower adjustment screws 86a, 86b are fixably attached. As the condyle engagement member 70 proximally advances toward the adjacent lateral knee condyle of the user from the lateral position, the condyle engagement member 70 and associated condyle pad 80 apply an increasing lateral proximally-directed dynamic linear force to the adjacent lateral knee condyle. The dynamic linear force is countered by an opposing (i.e., medial proximally-directed) static resistance force which is applied to the opposite medial knee condyle by the medial rotational hinge assembly 24. The static resistance force preferably has a lesser magnitude than the dynamic linear force due to the higher flexibility of the medial frame assembly. Accordingly, the sum of the linear forces to the knee joint results in application of a positive dynamic treatment force to the lateral knee condyle with respect to the lateral proximal direction, which has the desirable effect of reducing the load on the lateral compartment of the knee joint. The magnitude of the dynamic treatment force is directly related to the degree of outward telescoping of the upper and lower adjustment screws 86a, 86b, which is preferably expressed as a linear distance.

As noted above, rotational displacement of the adjustment wheel 120 in the first direction causes rotation of the display actuator gear 134 in the first direction, which in turn causes rotation of the display gear 122 in the second direction. The degree of rotation of the display gear 122 corresponds to the degree of outward telescoping of the upper and lower adjustment screws 86a, 86b. Accordingly, the user monitors the magnitude of the dynamic treatment force applied to the lateral knee condyle during practice of the hinge adjustment method by observing the position reference markings on the display gear 122 through the display window 144 of the hinge cover plate 50.

Rotational displacement of the adjustment wheel 120 in the second direction has the reverse effect to rotational displacement of the adjustment wheel 120 in the first direction as described above. In particular, rotational displacement of the adjustment wheel 120 in the second direction causes inward telescoping of the upper and lower adjustment screws 86a, 86b within the bores 112 of the upper and lower screw seats 88a, 88b, respectively, and correspondingly causes lateral distal linear displacement of the condyle engagement member 70. As the condyle engagement member 70 is drawn in the lateral distal direction away from the adjacent lateral knee condyle, the lateral proximally-directed dynamic linear force applied to the adjacent lateral knee condyle by the condyle engagement member 70 and associated condyle pad 80 decreases. Reduction of the dynamic treatment force to the lateral knee condyle with respect to the lateral proximal direction correspondingly increases the load on the lateral compartment of the knee joint.

It is apparent from the above-recited hinge adjustment method that the components of the rotation hinge assembly 22 preferably have specific dynamic or static characteristics in relation to one another. In particular, grouped hinge assembly components 50, 52, 54, 84, 88, 90, 92, 98, 120, 122 (as well as frame components 38, 40) are linearly static (i.e., linearly non-displaceable) with respect to one another. Grouped hinge assembly components 86, 70, 72 are likewise linearly static with respect to one another. However, the grouped hinge assembly components 86, 70, 72 are linearly dynamic (i.e., linearly displaceable) with respect to the grouped hinge assembly components 50, 52, 54, 84, 88, 90, 92, 98, 120, 122 (as well as frame components 38, 40). The term "linearly static" means that the linear spatial distance relationships between the commonly grouped components do not change at any time during the hinge adjustment method. The term "linearly dynamic" means that the linear spatial distance relationships between the commonly grouped components vary during the hinge adjustment method. Thus, the hinge components 86, 70, 72 are generally termed linear motion components and the hinge components 50, 52, 54, 84, 88, 90, 92, 98, 120, 122 are generally termed linear stationary components.

Grouped hinge assembly components 88, 90, 122 are rotationally static (i.e., rotationally non-displaceable) with respect to one another, grouped hinge assembly components 92, 120 are rotationally static with respect to one another, and grouped hinge assembly components 50, 52, 54, 70, 72, 86 are rotationally static with respect to one another. However, the grouped hinge assembly components 88, 90, 122 and the grouped hinge components 92, 120 are both rotationally dynamic (i.e., rotationally displaceable) with respect to the grouped hinge assembly components 50, 52, 54, 70, 72, 86. The term "rotationally static" means that rotational spatial distance relationships between the commonly grouped components do not change at any time during the hinge adjustment method. The term "rotationally dynamic" means that the rotational spatial distance relationships between the commonly grouped components vary during the hinge adjustment method. Thus, the hinge components 88, 90, 92, 120, 122 are generally termed rotational motion components and the hinge components 50, 52, 54, 70, 72, 86 are generally termed rotational stationary components.

Although the lateral hinge assembly 22 of the rotationally-hinged frame 12 described above enables the osteoarthritis treatment function, while the medial rotational hinge assembly 24 lacks the osteoarthritis treatment function, it is alternatively within the scope of the present invention to reverse the hinge assemblies on the frame so that the medial hinge assembly has structure enabling the osteoarthritis treatment function, while the lateral rotational hinge assembly is a conventional rotational hinge assembly lacking such structure. It is apparent that this embodiment of a frame configuration enables application of a medial proximally-directed dynamic linear treatment force to the knee joint which has the desirable effect of reducing the load on the medial compartment of the knee joint.

In yet another alternative, it is within the scope of the present invention to reconfigure the rotationally-hinged frame so that both the lateral and medial hinge assemblies have structure which enables selective application of a treatment force to the adjacent knee condyle on either side of the knee joint. The sum of the treatment forces to the adjacent knee condyles can be balanced or unbalanced by the user in accordance with the teaching herein, depending on the desired treatment application and the requirements of the user.

While the forgoing preferred embodiments of the invention have been described and shown, it is understood that alternatives and modifications, such as those suggested and others, may be made thereto and fall within the scope of the invention.

We claim:

1. A hinge assembly for a knee brace comprising:
   first and second screw seats, wherein each said screw seat has a bore and an internal thread in said bore;
   first and second screw seat gears having first and second rotary seat gear teeth respectively, wherein said first screw seat gear is fixably connected to an end of said first screw seat and said second screw seat gear is fixably connected to an end of said second screw seat and further wherein said first screw seat rotates in with rotation of said first screw seat gear and said second screw seat rotates in with rotation of said second screw seat gear such that said first and second screw seats and said first and second screw seat gears are rotationally static with respect to one another;
   an adjustment actuator gear having rotary actuator gear teeth engaging said first and second rotary seat gear teeth, thereby enabling said first and second screw seat gears to rotate in response to rotation of said adjustment actuator gear;
   first and second adjustment screws, wherein each said adjustment screw has an external thread and further wherein said first adjustment screw is positioned in said bore of said first screw seat with said external thread threaded into said internal thread of said bore and said second adjustment screw is positioned in said bore of said second screw seat with said external thread threaded into said internal thread of said bore, thereby enabling outward or inward telescoping of said first and second adjustment screws within said bores of said first and second screw seats, respectively, in response to rotation of said adjustment actuator gear, further wherein said first and second adjustment screws are rotationally dynamic with respect to said first and second screw seats and said first and second screw seat gear; and
   a condyle engagement member, wherein said first and second adjustment screws are connected to said condyle engagement member, thereby enabling proximal displacement of said condyle engagement member in response to outward telescoping of said first and second adjustment screws and enabling distal displacement of said condyle engagement member in response to inward telescoping of said first and second adjustment screws.

2. The hinge assembly of claim 1 further comprising a hinge support plate rotatably connected to said first and second screw seats such that said hinge support plate and said first and second screw seats are rotationally dynamic with respect to one another.

3. The hinge assembly of claim 2, wherein said adjustment actuator gear rotatably engages said hinge support plate such that said hinge support plate and said adjustment actuator gear are rotationally dynamic with respect to one another.

4. The hinge assembly of claim 1 further comprising an actuator wheel and a display actuator gear, wherein said adjustment actuator gear and said display actuator gear are fixably positioned on said actuator wheel such that said actuator wheel, said display actuator gear, and said adjustment actuator gear are rotationally static with respect to one another and said display actuator gear and said adjustment actuator gear rotate in with rotation of said actuator wheel.

5. The hinge assembly of claim 4 further comprising a rotary display gear having position reference markings thereon and engaging said display actuator gear, wherein said display gear rotates in response to rotation of said display actuator gear.

6. The hinge assembly of claim 1 further comprising a manually rotatable adjustment wheel, wherein said adjustment wheel is connected to said adjustment actuator gear and further wherein said adjustment actuator gear rotates in response to rotation of said actuator wheel.

7. The hinge assembly of claim 2, wherein said hinge support plate is a first hinge support plate, said hinge assembly further comprising a second hinge support plate and a hinge cover plate, wherein said hinge cover plate is positioned on the opposite side of said hinge assembly from said condyle engagement member and in cooperation with said second hinge support plate covers said adjustment actuator gear.

8. A hinge assembly for a knee brace comprising:
a screw seat having a screw seat thread;
a screw seat gear fixably connected to said screw seat, wherein said screw seat and said screw seat gear are rotationally static with respect to one another such that said screw seat rotates in with rotation of said screw seat gear; and
an adjustment screw having an adjustment screw thread engaging said screw seat thread, thereby enabling inward or outward linear displacement of said adjustment screw relative to said screw seat in response to rotation of said screw seat gear, wherein said adjustment screw is rotationally dynamic with respect to said screw seat and said screw seat gear.

9. The hinge assembly of claim 8 further comprising a condyle engagement member, wherein said adjustment screw is connected to said condyle engagement member, thereby enabling proximal displacement of said condyle engagement member in response to outward displacement of said adjustment screw and enabling distal displacement of said condyle engagement member in response to inward displacement of said adjustment screw.

10. The hinge assembly of claim 8 further comprising a hinge support plate rotatably connected to said screw seat such that said hinge support plate and said screw seat are rotationally dynamic with respect to one another.

11. The hinge assembly of claim 8 further comprising an adjustment actuator gear having rotary actuator gear teeth engaging rotary seat gear teeth of said screw seat gear, thereby enabling said screw seat gear to rotate in response to rotation of said adjustment actuator gear.

12. The hinge assembly of claim 11, wherein said adjustment actuator gear rotatably engages a hinge support plate rotatably connected to said screw seat such that said hinge support plate, said adjustment actuator gear, and said screw seat are rotationally dynamic with respect to one another.

13. The hinge assembly of claim 11 further comprising an actuator wheel and a display actuator gear, wherein said adjustment actuator gear and said display actuator gear are fixably positioned on said actuator wheel such that said actuator wheel, said display actuator gear, and said adjustment actuator gear are rotationally static with respect to one another and said display actuator gear and said adjustment actuator gear rotate in with rotation of said actuator wheel.

14. The hinge assembly of claim 13 further comprising a rotary display gear having position reference markings thereon and engaging said display actuator gear, wherein said display gear rotates in response to rotation of said display actuator gear.

15. The hinge assembly of claim 13 further comprising a manually rotatable adjustment wheel, wherein said adjustment wheel is connected to said adjustment actuator gear and further wherein said adjustment actuator gear rotates in response to rotation of said actuator wheel.

16. A hinge assembly for a knee brace comprising:
a screw seat having a screw seat thread;
a screw seat gear fixably connected to said screw seat, wherein said screw seat and said screw seat gear are rotationally static with respect to one another such that said screw seat rotates in with rotation of said screw seat gear;
an adjustment screw having an adjustment screw thread engaging said screw seat thread, thereby enabling inward or outward linear displacement of said adjustment screw relative to said screw seat in response to rotation of said screw seat gear, wherein said adjustment screw is rotationally dynamic with respect to said screw seat and said screw seat gear;
a condyle engagement member, wherein said adjustment screw is connected to said condyle engagement member, thereby enabling proximal displacement of said condyle engagement member in response to outward displacement of said adjustment screw and enabling distal displacement of said condyle engagement member in response to inward displacement of said adjustment screw; and
a displacement indicator displaying a degree of proximal or distal displacement of said condyle engagement member.

17. The hinge assembly of claim 16 further comprising an adjustment actuator gear having rotary actuator gear teeth engaging rotary seat gear teeth of said screw seat gear, thereby enabling said screw seat gear to rotate in response to rotation of said adjustment actuator gear.

18. The hinge assembly of claim 17 further comprising an actuator wheel and a display actuator gear, wherein said adjustment actuator gear and said display actuator gear are fixably positioned on said actuator wheel such that said actuator wheel, said display actuator gear, and said adjustment actuator gear are rotationally static with respect to one another and said display actuator gear and said adjustment actuator gear rotate in with rotation of said actuator wheel.

19. The hinge assembly of claim 18 further comprising a rotary display gear having position reference markings thereon and engaging said display actuator gear, wherein said displacement indicator includes said display gear and said display gear rotates in response to rotation of said display actuator gear.

20. The hinge assembly of claim 17 further comprising a manually rotatable adjustment wheel, wherein said adjustment wheel is connected to said adjustment actuator gear and further wherein said adjustment actuator gear rotates in response to rotation of said actuator wheel.

* * * * *